United States Patent [19]
Fischer

[11] Patent Number: 5,985,249
[45] Date of Patent: *Nov. 16, 1999

[54] STICKY DENTAL COMPOSITIONS FOR ADHERING A PASSIVE-TYPE DENTAL TRAY OVER A PERSON'S TEETH

[75] Inventor: Dan E. Fischer, Sandy, Utah

[73] Assignee: Ultradent Products, Inc., South Jordan, Utah

[ * ] Notice: This patent is subject to a terminal disclaimer.

[21] Appl. No.: 08/949,892

[22] Filed: Oct. 14, 1997

Related U.S. Application Data

[63] Continuation-in-part of application No. 08/865,910, May 30, 1997, Pat. No. 5,851,512, and a continuation-in-part of application No. 08/722,549, Sep. 27, 1996, Pat. No. 5,725,843, which is a continuation of application No. 08/378,315, Jan. 25, 1995, Pat. No. 5,770,182, which is a continuation of application No. 08/099,247, Jul. 28, 1993, abandoned, which is a continuation of application No. 07/985,700, Dec. 2, 1992, abandoned, which is a continuation of application No. 07/718,210, Jun. 20, 1991, abandoned, which is a division of application No. 07/497,934, Mar. 22, 1990, abandoned.

[51] Int. Cl.⁶ ............... A61K 7/16; A61C 5/00
[52] U.S. Cl. ............... 424/49; 424/52; 424/53; 424/673; 514/900; 514/944; 433/215
[58] Field of Search ............... 424/49, 53, 52, 424/673; 514/900, 944; 433/215; 106/35

[56] References Cited

U.S. PATENT DOCUMENTS

| | | |
|---|---|---|
| Re. 28,667 | 12/1975 | Gores ............... 128/136 |
| Re. 34,196 | 3/1993 | Munro ............... 433/215 |
| 165,584 | 7/1875 | Hopfen . |
| 767,553 | 8/1904 | Edgelow . |
| 803,472 | 10/1905 | Dennis . |
| 803,474 | 10/1905 | Dennis . |
| 1,371,029 | 3/1921 | Jennings . |
| 1,642,653 | 9/1927 | Goldstein . |

(List continued on next page.)

FOREIGN PATENT DOCUMENTS

| | | |
|---|---|---|
| 0 286 766 | 10/1988 | European Pat. Off. . |
| 0 325 267 | 7/1989 | European Pat. Off. . |
| 1 489 712 | 11/1965 | Germany . |
| 1 566 227 | 10/1969 | Germany . |
| 28 48 237 | 11/1978 | Germany . |
| 8100383 | 8/1982 | Netherlands . |
| 528007 | 12/1983 | Spain . |

OTHER PUBLICATIONS

Zioner, Doron D. et al. "Controlled Study of the Clinical Effectiveness of a New Oxygen Gel on Plaque, Oral Debris and Gingival Inflammation", *Pharmacology and Therapeutics in Dentistry*, vol. 1, pp. 7–15 (Oct. 1970).

Amigoni et al., "The Use of Sodium Bicarbonate and Hydrogen Peroxide Periodontal Therapy: A Review", *JADA*, vol. 114, pp. 217–221 (Feb. 1987).

Archambault, Dr. Gregory A., "Home Bleaching" *Nation–Wide Dental*, vol. 22, No. 22, Jan. 1990.

Arens, Donald E. et al., "A Practical Method of Bleaching Tetracycline–Stained Teeth", *Oral Surg., Oral Med., Oral Path.* vol. 34 (No. 5), Nov. 1972.

(List continued on next page.)

*Primary Examiner*—Raj Bawa
*Attorney, Agent, or Firm*—Workman, Nydegger, Seeley

[57] ABSTRACT

Sticky dental compositions which include a sticky, glue-like matrix material for treating a variety of tooth or gum ailments, and methods for treating teeth using such compositions. For maximum comfort, an improved dental tray that is thin-walled, flexible and lightweight is used to hold the sticky dental composition adjacent the desired tooth surfaces. The sticky dental compositions include a sticky matrix material into which is dispersed an appropriate dental agent, such as a bleaching agent, a desensitizing agent, and an anticariogenic agent, an antimicrobial agent. The matrix material preferably includes carboxypolymethylene that has been partially neutralized with a base to reduce etching of the enamel. The carboxypolymethylene adds a unique stickiness to the dental composition which helps to adhere and retain the soft tray material against the person's teeth.

22 Claims, 2 Drawing Sheets

U.S. PATENT DOCUMENTS

| | | | |
|---|---|---|---|
| 1,691,785 | 11/1928 | Remensnyder . | |
| 1,818,146 | 8/1931 | Maker . | |
| 1,934,688 | 11/1933 | Ackerman | 32/5 |
| 2,257,709 | 9/1941 | Anderson | 128/260 |
| 2,669,988 | 2/1954 | Carpenter | 128/136 |
| 2,798,053 | 7/1957 | Brown | 260/2.2 |
| 2,835,628 | 5/1958 | Saffir | 167/84 |
| 2,858,281 | 10/1958 | Bauman et al. | 260/2.2 |
| 2,923,692 | 2/1960 | Ackerman et al. | 260/17.4 |
| 2,985,625 | 5/1961 | Jones | 260/78 |
| 3,060,935 | 10/1962 | Riddell | 128/260 |
| 3,073,300 | 1/1963 | Berghash | 128/136 |
| 3,107,668 | 10/1963 | Thompson | 128/136 |
| 3,224,441 | 12/1965 | Monaghan | 128/136 |
| 3,224,443 | 12/1965 | Monaghan | 128/136 |
| 3,234,942 | 2/1966 | Simor | 128/172.1 |
| 3,247,844 | 4/1966 | Berghash | 128/136 |
| 3,250,272 | 5/1966 | Greenberg | 128/136 |
| 3,319,626 | 5/1967 | Lindsay | 128/136 |
| 3,339,547 | 9/1967 | Drabkowski | 128/260 |
| 3,379,193 | 4/1968 | Monaghan | 128/136 |
| 3,380,446 | 4/1968 | Martin | 128/24 |
| 3,385,291 | 5/1968 | Martin | 128/62 |
| 3,399,457 | 9/1968 | Hagman | 32/19 |
| 3,416,527 | 12/1968 | Hoef | 128/260 |
| 3,448,738 | 6/1969 | Berghash | 128/136 |
| 3,481,329 | 12/1969 | Warren, Jr. | 128/66 |
| 3,499,844 | 3/1970 | Kibbel et al. | 252/316 |
| 3,505,995 | 4/1970 | Greenberg | 128/136 |
| 3,527,218 | 9/1970 | Westine | 128/229 |
| 3,527,219 | 9/1970 | Greenberg | 128/260 |
| 3,536,069 | 10/1970 | Gores | 128/136 |
| 3,567,823 | 3/1971 | Yamaga | 424/132 |
| 3,624,909 | 12/1971 | Greenberg | 32/40 |
| 3,625,215 | 12/1971 | Quisling | 128/260 |
| 3,657,413 | 4/1972 | Rosenthal | 424/81 |
| 3,688,406 | 9/1972 | Porter et al. | 320/40 R |
| 3,742,942 | 7/1973 | Westline | 128/62 |
| 3,844,286 | 10/1974 | Cowen | 128/260 |
| 3,911,104 | 10/1975 | Harrison | 424/52 |
| 3,955,281 | 5/1976 | Weitzman | 32/14 |
| 3,969,499 | 7/1976 | Lee, Jr. et al. | 424/52 |
| 3,976,223 | 8/1976 | Jass et al. | 222/94 |
| 3,988,433 | 10/1976 | Benedict | 424/53 |
| 3,998,945 | 12/1976 | Vit | 424/53 |
| 4,032,627 | 6/1977 | Suchan et al. | 424/54 |
| 4,044,762 | 8/1977 | Jacobs | 128/136 |
| 4,064,628 | 12/1977 | Weitzman | 32/14 |
| 4,138,814 | 2/1979 | Weitzman . | |
| 4,164,940 | 8/1979 | Quinby | 128/62 |
| 4,173,219 | 11/1979 | Lentine | 128/260 |
| 4,173,505 | 11/1979 | Jacobs | 156/285 |
| 4,239,818 | 12/1980 | LaBate | 427/236 |
| 4,244,942 | 1/1981 | Kamishita et al. | 424/81 |
| 4,251,507 | 2/1981 | Olson | 424/49 |
| 4,302,441 | 11/1981 | Muhlemann et al. | 424/48 |
| 4,376,628 | 3/1983 | Aardse | 433/80 |
| 4,419,992 | 12/1983 | Chorbajian | 128/136 |
| 4,428,373 | 1/1984 | Seid et al. | 604/77 |
| 4,431,631 | 2/1984 | Clipper et al. | 424/53 |
| 4,518,721 | 5/1985 | Dhabhar et al. | 523/120 |
| 4,522,805 | 6/1985 | Gordon | 424/52 |
| 4,522,806 | 6/1985 | Muhlemann et al. . | |
| 4,528,180 | 7/1985 | Schaeffer | 424/52 |
| 4,537,778 | 8/1985 | Clipper et al. | 424/53 |
| 4,544,354 | 10/1985 | Gores et al. | 433/42 |
| 4,557,692 | 12/1985 | Chorbajian | 433/215 |
| 4,560,351 | 12/1985 | Osborne | 433/80 |
| 4,568,536 | 2/1986 | Kronenthal et al. | 424/22 |
| 4,592,487 | 6/1986 | Simon et al. | 222/94 |
| 4,592,488 | 6/1986 | Simon et al. | 222/94 |
| 4,661,070 | 4/1987 | Friedman | 433/203.1 |
| 4,687,663 | 8/1987 | Schaeffer | 424/52 |
| 4,696,757 | 9/1987 | Blank et al. | 252/186.29 |
| 4,755,386 | 7/1988 | Hsiao et al. | 424/435 |
| 4,770,634 | 9/1988 | Pellico | 433/217 |
| 4,788,052 | 11/1988 | Ng et al. | 424/53 |
| 4,812,308 | 3/1989 | Winston et al. | 424/52 |
| 4,839,156 | 6/1989 | Ng et al. | 424/53 |
| 4,839,157 | 6/1989 | Mei-King Ng et al. | 424/53 |
| 4,849,213 | 7/1989 | Schaeffer | 424/53 |
| 4,895,721 | 1/1990 | Drucker | 424/53 |
| 4,902,227 | 2/1990 | Smith | 433/215 |
| 4,939,284 | 7/1990 | Degenhardt | 558/142 |
| 4,954,487 | 9/1990 | Cooper et al. | 514/159 |
| 4,966,777 | 10/1990 | Gaffab et al. . | |
| 4,968,251 | 11/1990 | Darnell | 433/216 |
| 4,971,782 | 11/1990 | Rudy et al. | 424/53 |
| 4,980,152 | 12/1990 | Frazier et al. | 424/52 |
| 4,983,379 | 1/1991 | Schaeffer | 424/52 |
| 4,983,381 | 1/1991 | Torres Zaragoza | 424/53 |
| 4,988,500 | 1/1991 | Hunter et al. | 424/53 |
| 4,990,089 | 2/1991 | Munro | 433/215 |
| 5,009,885 | 4/1991 | Yarborough | 424/53 |
| 5,059,417 | 10/1991 | Williams et al. | 424/53 |
| 5,076,791 | 12/1991 | Madray, Jr. | 433/215 |
| 5,084,268 | 1/1992 | Thaler | 424/53 |
| 5,098,303 | 3/1992 | Fischer | 433/215 |
| 5,122,365 | 6/1992 | Murayama . | |
| 5,165,242 | 11/1992 | Silverman | 128/861 |
| 5,234,342 | 8/1993 | Fischer | 433/215 |
| 5,356,291 | 10/1994 | Darnell | 433/216 |
| 5,376,006 | 12/1994 | Fischer | 424/53 |
| 5,401,495 | 3/1995 | Murayama . | |
| 5,409,631 | 4/1995 | Fischer | 424/53 |
| 5,472,704 | 12/1995 | Samtus et al. | 424/435 |
| 5,505,933 | 4/1996 | Norfleet et al. | 424/52 |
| 5,522,726 | 6/1996 | Hodosh | 433/215 |
| 5,575,655 | 11/1996 | Darnell | 433/216 |
| 5,631,000 | 5/1997 | Pellico . | |
| 5,725,843 | 3/1998 | Fischer | 424/49 |
| 5,746,598 | 5/1998 | Fischer | 424/53 |
| 5,770,182 | 6/1998 | Fischer | 424/49 |

OTHER PUBLICATIONS

Arzt, Alvin H, "Updating Tetracycline–Stained Teeth Bleaching Technique", *Quintessence International,* Jan. 1981, No. 1, pp. 15–18.

Attin et al., "Die Bleichbehandlung–ein fester Bestandteil ästhetischer Zahnheilkunde," Universitätsklinik für Abt. Poliklinik, Hugstetter Str. 55, 79016 Freiburg—Attin et al., "Bleaching—An Essential Part of Esthetic Dentistry," University Clinic for Dentistry, Oral Medicine and Orthodontics, Polyclinic, Hugstetter Str. 55, D–79106 Freiburg, 1995.

BF Goodrich Chemical (Deutschland) GmbH: Carbopol$^R$, Wasserloösliche Polymere–Carbopol™, Water Soluble Polymer, 1984.

Baumgartner, J. Craig et al., "Human Pulpal Reaction to the Modified McInnes Bleaching Technique", *Journal of Endodontics,* vol. 9, No. 12, Dec. 1983, pp. 527–529.

Bayless, J. Mark et al., "Diagnosis and Treatment of Acute Fluoride Toxicity", *JADA,* vol. 110, Feb. 1985, pp. 209–211.

Blaine, Edward et al., "Oral Hygiene Supplement for Handicapped Children," *The Journal of Dental Practice,* pp. 29–31 (May 1971).

Bouscher, Charles F., "Bleaching Fluorosis Stained Teeth", *New Mexico Dental Journal,* vol. 16, No. 1, May 1965, pp. 33–34.

Bowles, William H. et al., "Pulp Chamber Penetration by Hydrogen Peroxide Following Vital Bleaching Procedures" *Journal of Endodontics,* vol. 13, No. 8, Aug. 1987, pp. 375–377.

Budaveri, S. et al., "The Merck Index," *Merck & Co., Inc.,* pp. 323, 1449 and 1450 (1989).

Budaveri, S. et al., "The Merck Index," *Merck & Co., Inc.,* pp. 1521, 1536, 1537, MISC–3 and 4, CI–337 (1989).

Buffalo Dental Mfg. Co. Technical for Sta–Vac mini–lab vacuum adapter, Brochure No. 895/01.

Christensen, Gordon J. et al., "Bleaching Vital Tetracycline Stained Teeth", *Quintessence International,* vol. 9, No. 6, Jun. 1978.

Cobe, Herbert J. et al, "Urea Peroxide . . . in Glycerine", *Pennsylvania Dental Journal,* vol. 25, No. 4, pp. 12–18 (Jan. 1959).

Cohen, Stephen, "A Simplified Method for Bleaching Discolored Teeth," *Digest,* pp. 301–303 (Jul. 1968).

Cohen et al., "Bleaching Tetracycline–Stained Vital Teeth", *Oral Surgery,* vol. 29, No. 3, pp. 465–471 (Mar. 1970).

Cohen, Steven et al. "Human Pulpal Response to Bleaching Procedures on Vital Teeth", *Journal of Endodontics,* vol. 5, No. 5, May 1979, pp. 134–138.

Colon, P.G. Jr., "Removing Fluorosis Stains From Teeth", *Quintessence International,* vol. 2, No. 6, pp. 89–93, Jun. 1971.

Compton, Duane E., "Bleaching of Tetracycline–Stained Vital Teeth", *Journal of Endodontics,* vol. 5, No. 4, May 1979.

Corcoran, John F. et al., "Bleaching of Vital Tetracycline Stained Teeth", *Journal of the Michigan Dental Association,* vol. 56, No. 12, Dec. 1974, pp. 340–343.

Croll, Theodore P. et al, "Enamel Color Modification By Controlled Hydrochloric Acid–Pumice Abrasion. I. Technique and Examples" *Quintessence International,* vol. 17, No. 2, 1986.

Croll, Theodore P. et al., "A Case of Enamel Color Modification: 60 year Results" *Quintessence International* ovl. 18, No. 7, 1987, pp. 493–495.

Cvek, Miomir et al, "External Root Resorption Following Bleaching of Pulpless Teeth With Oxygen Peroxide", *Endod. Dent. Traumatol,* 1985 vol. 1, pp. 56–60.

Darnell, Daniel H. et al., "Vital Tooth Bleaching: The White & Brite Technique," *Compend. Cont. Educ. Dent.,* vol. XI, No. 2, pp. 86–94, Feb. 1990.

Davies, A.K. et al., Photo–oxidation of Tetracycline Absorbed on Hydroxyapatite in Relation to the Light–Induced Staining of Teeth, *Material Science,* J. Dent, Res., vol. 64, No. 6, pp. 936–939, Jun. 1985.

*Dental Pharmacology,* pp. 296–297 (Mar. 21, 1990).

Dickstein, Benjamin, "Neonatal Oral Candidiasis: Evaluation of a New Chemotherapeutic Agent," *Clinical Pediatrics,* pp. 485–488 (Aug. 1964).

Dietz, Ellen Roberta, "Bleaching Vital Teeth", *The Dental Assistant,* Jan./Feb. 1988, pp. 7–8.

Drew, Claudine Paula, "Teeth Bleaching . . . A Vital Technique For You To Know", *Dental Assisting,* Sep./Oct. 1988, pp. 23–25.

Ekstrand, Jan et al., "Systemic Fluoride Absorption Following Fluoride Gel Application," *J. Dent. Res.,* vol. 59, No. 6, p. 1067 (Jun. 1980).

Englander et al., "The Prevention of Dental Caries in the Syrian Hamster after Repeated Topical Application of Sodium Fluoride Gels", *JADA,* vol. 73, pp. 1342–1347 (Dec. 1966).

Fasanaro, Tom S., *Bleaching Teeth: History, Chemicals, and Methods Used for Comong Tooth Discolorations* (Jan. 1991, 2nd Ed.).

Feiglin, Barry, "A 6–year Recall Study of Clinical Chemically Bleached Teeth," *Oral Surg, Oral Med. Oral Pathol,* vol. 63, pp. 610–613 (May 1987).

Feinman, Ronald A., "A Combination Therapy" *CDA Journal,* Apr. 1987, pp. 10–13.

Feinman et al., "Chemical, Optical, and Physiologic Mechanisms of Bleaching Products: A Review," *The Bleaching Report,* vol. 3, pp. 32–37, 1991.

Feinman, Ronald A., "A Matrix Vital Bleaching: A Review" *Esthetic Dentistry Update,* vol. 2, No. 3, Jun. 1991, pp. 42–47.

Feinman, Ronald A., "History of Bleaching Nonvital Teeth" *Bleaching: A New Addition to the Esthetic Dentistry Armamentarium,* 1990, pp. 11–12.

Fields, John P. "Intracoronal Bleaching of Tetracycline–Stained Teeth: A Case Report" *Journal of Endodontics,* vol. 8, No. 11, Nov. 1982, pp. 512–513.

Firestone, A.R. et al., "Effect of Topical Application of Urea Peroxide on Caries Incidence and Plaque Accumulation in Rats," *Caries Res.,* vol. 16, pp. 112–117 (1982).

Fogel, Maxwell S., et al., "Use of an Antiseptic Agent in Orthodontic Hygiene," *Dental Survey,* pp. 50–54 (Oct. 1971).

Franchi, Gene J., "A Practical Technique for Bleaching Discolored Crowns of Young Permanent Incisors," *Journal of Dentistry for Children,* vol. 64, No. 6, pp. 936–939, Jun. 1985.

Freedman, George A., "The Safety of Tooth Whitening," *Dentistry Today,* pp. 32–35 (Apr. 1990).

Friedman et al., "Incidence of External Root Resorption and Esthetic Results in 58 Bleached Pulpless Teeth," *Endod. Dental Traumatol.,* pp. 23–26 (Jun. 1987).

Gallion et al. "Vital Bleaching, Effects on Brightness", Alumni Dental Convention, Loma Linda University School of Dentistry (1990).

Genesis 2000 advertisement for "Genesis White" whitening system (to the best of Applicant's knowledge an belief, this reference was published at least as early as Mar. 21, 1990).

Gertenrich et al., "Treatment of Dilantin Gingival Hyperplasia with Proxigel," *American Journal of Mental Deficiency,* vol. 78, No. 4, pp. 502–504 (1974).

Goldstein, Ronald E., "Bleaching Teeth: New Materials—New Role", *JADA* Special Issue, Dec. 1987, pp. 44–52.

Grogan, David Francis, "Agents Used in Bleaching Teeth", *Tufts Dental Outlook,* vol. 20, No. 1, Mar., 1946, pp. 20–23.

Hardman, Patrick K. et al., "Stability of Hydrogen Peroxide As a Bleaching Agent", *General Dentistry,* Mar./Apr. 1985, pp. 121–122.

Harrington, Gerald W. et al, "External Resorption associated with bleaching of pulpless teeth", *Journal of Endodontics,* vol. 5, No. 11, Nov. 1979, pp. 344–348.

Haywood, Van B. et al., "Nightguard Vital Bleaching", *Quinessence International,* vol. 20, No. 3, pp. 173–176 (1989).

Haywood, Van B. et al., "Nightguard Vital Bleaching: Effects on Enamel Surface Texture and Diffusion", *Quintessence International,* vol. 21, No. 10, (1990), pp. 801–804.

Haywood, Van B. "Letter to the Editor", *Quintessence International,* vol. 20, No. 10, (1989), p. 697.

Heller, L., "Is Youir Dentist Up–To–Date?", *Redbook,* pp. 20–26 (Mar. 1990).

Horii, A.A., et al., "A Vinyl Applicator for Assessing Drugs in the Treatment of Caries and Periodontal Disease in the Hamster," Laboratory of Histology and Pathology, National Institute of Dental Research, National Institutes of Health, Department of Health, Education, and Welfare, U.S. Publich Health Service, Bethesda Maryland, p. 152 (submitted for publication Aug. 29, 1963).

Jordan, Ronald E., et al., "Conservative Vital Bleaching Treatment of Discolored Dentition", *Compendium*, vol. V, No. 10, Nov./Dec. 1984, pp. 803–808.

Jordan, Ronald E., et al., "Conservative Applications of Acid Etch–Resin Techniques", *Dental Clinics of North America*, vol. 25, No. 2, Apr. 1981, pp. 307–337.

Kaslik, Ralph S., "Studies on the Effects of a Urea Peroxide Gel on Plaque Formation and Gingivitis," *J. Periodontol.*, pp. 230–232 (Apr. 1975).

Kehoe, Joseph C., "Bleaching Today", *Florida Dental Journal*, vol. 55, No. 1, Spring 1984, pp. 12–15.

Kennedy, Nathaniel, "The Tetracycline Dilemma and a Vital Bleaching Technique", *CDS Review*, vol. 69, No. 5, May 1976, pp. 28–30.

Kesling, Harold D., "The Tooth Positioner as the Means of Final Positioning of Teeth to a Predetermined Pattern," *Journal of Dentistry for Children*, pp. 103–105.

Kirkegaard et al., "Children's Response to Various Local Fluoride Treatments", *Acta Odontol. Scand.*, vol. 38, No. 4, pp. 235–240 (1980).

Kundergren et al., "In Vivo and In Vitro Studies on a New Peroxide–Containing Toothpaste", *Scand. J. Dent. Res.*, vol. 81, pp. 544–547 (1973).

LeCompte, E.J. et al., "Oral Fluoride Retention Following Various Topical Application Techniques in Children," *J. Dent. Res.*, vol. 61, No. 12, pp. 1397–1400 (1982).

Ledoux, William R., et al., "Structural Effects of Bleaching On Tetracycline–Stained Vital Rat Teeth", *The Journal of Prosthetic Dentistry*, Jul. 1985, vol. 54, No. 1, pp. 55–59.

Lowney, Jeremiah, J., "A Simplified Technique for Bleaching a Discolored Tooth," *Dental Digest*, pp. 446–448 (Oct. 1964).

McEvoy, S., "Chemical Agents for Removing Intrinsic Stains from Vital Teeth. II. Current Techniques and Development", *Quintessence International*, vol. 20, No. 5, pp. 323–328 (1989).

McEvoy, S., "Chemical Agents for Removing Intrinsic Stains from Vital Teeth. II. Current Techniques and their Clinical Application", *Quintessence International*, vol. 20, No. 6, pp. 379–384 (1989).

McMurray, Crawford A., "Removal of Stains From Mottled Enamel Teeth", *Texas Dental Journal*, vol. 59, No. 9, Sep. 1941.

Mello, Hilton S., "The Mechanism of Tetracycline Staining in Primary and Permanent Teeth", *Dentistry for Children*, vol. 34, No. 6, pp. 478–487, Nov. 1967.

Merwe, P.K. v.d., "The Reomoval Of the Stain From Mottled Teeth", *The South African Dental Journal*, vol. 18, No. 2, Feb. 1944, pp. 31–34.

Morrison, Scott W., "Vital Tooth Bleaching—The Patient's Viewpoint", *General Dentistry*, May–Jun. 1986, pp. 238–240.

Murrin, James R., et al., "Chemical Treatment of Vital Teeth With Intrinsic Stain", *OJD*, Nov. 1982, pp. 6–10.

Myers, Malcolm, et al., "Effect of Daily Application of Fluoride in a Custom Fitted Mouthpiece on Plaque Flora Associated with Dental Decay", *Journal of Dental Research*, vol. 50, No. 3, pp. 597–599 (May 1971).

Nathanson, Dan et al., "Bleaching Vital Teeth: A Review and Clinical Study" *Compend Contin. Educ. Dent.* vol. VIII, No. 7, pp. 490–498, Jul./Aug. 1987.

Newbrun, E., Topical Fluoride Therapy: Discussion of Some Aspects of Toxicology, Safety, and Efficacy, *J. Dent. Res.*, vol. 66, No. 5, pp. 1084–1086 (1987).

Nutting, Edwin B., et al., "Chemical Bleaching of Discolored Endodontically Treated Teeth", *Dental Clinics of North America*, Nov. 1967, pp. 655–662.

Prinz, Herman, "Recent Improvements in Tooth Bleaching", *The Dental Cosmos*, vol. 66, pp. 558–560 (May 1924).

Reddy, J. et al., "The Effect of a Urea Peroxide Rinse on Dental Plaque and Gingivitis," *J. Periodontol.*, pp. 607–610 (Oct. 1976).

Rees, Terry D. et al., "Oral Ulcerations with Use of Hydrogen Peroxide," *J. Periodontol.*, pp. 689–692 (1986).

Reid, J.S., et al. "A Suggested Method of Bleaching Tetracycline–Stained Vital Teeth", *British Dental Journal*, vol. 142, No. 8, Apr. 1977, p. 261.

Reid, J.S., "Patient Assessment of The Value of Bleaching Tetracycline–Stained Teeth", *Journal of Dentistry For Children*, Sep./Oct. 1985, pp. 353–355.

Rethman, Jill, "At Home Tooth Bleaching: A Review for the Dental Professional", *J. Practice Hygiene*, pp. 1–5, May/Jun. 1994).

Richardson, Sue Ellen, "Home Bleaching: Effectiveness, History, Technique, Bleaches, Cost and Safety," *J. Greater Houston Dent. Soc.*, pp. 22–25 (Nov. 1989).

Ripa, Louis W. et al., "Effect of Prior Toothcleaning on Biannual Professional APF Topical Fluoride Gel–tray Treatments", *Clinical Preventive Dentistry*, vol. 5, No. 4, Jul.–Aug. 1983.

Ripa, Louis W. et al., "Effect of Prior Toothcleaning on Biannual Professional Acidulated Phosphate Fluoride Topical Fluoride Gel–tray Treatments—Results After Three Years", *Caries Res.* 18: 457–464 (1984).

Seale, N.S. et al., "Systematic Assessment of Color Removal Following Vital Bleaching of Intrinsically Stained Teeth," *J. Dent. Res.*, vol. 64, No. 3, pop. 457–461 (1985).

Shapiro, William B., et al., "The Influence of Urea Peroxide Gel on Plaque, Calculus and Chronic Gingival Inflammation," *J. Periodontology*, pp. 636–639 (Oct. 1973).

Shipman, B., et al., "The Effect of a Urea Peroxide Gel on Plaque Deposits and Gingival Status," *J. Periodont.*, pp. 283–285 (1971).

Simon, James F. et al., *"Efficacy of Vital Home Bleaching"* CDA Journal (Jan. 1993).

Smith et al., "Further Studies on Methods of Removing Brown Stain from Mottled Teeth", *JADA*, vol. 29, pp. 571–576 (Apr. 1942).

Spasser, Herbert F. "A Simple Bleaching Technique Using Sodium Perborate", *New York State Dental Journal*, No. 27, Aug.–Sep. 1961, pp. 332–334.

Spencer, Duane E., "A Conservative Method of Treating Tetracycline Stained Teeth", *ASBC Journal of Dentistry For Children*, vol. 29, No. 6, Nov./Dec. 1972, pp. 25–28.

Stewart, George G. et al., "A Study of a New Medicament in the Chemomechanical Preparation of Inflected Root Canals," *The Journal of the American Dental Association*, vol. 63, pp. 33–37 (Jul. 1961).

Stindt, Diana J. e tal., "An Overview of Gly–Oxide Liquid in Control and Prevention of Dental Disease," *Compend. Contin. Educ. Dent.*, vol. X, No. 9, pp. 514–519, Sep. 1989.

Swift, Edward J. Jr., "A Method For Bleaching Discolored Vital Teeth", *Quintessence International*, vol. 19, No. 9, 1988, pp. 607–612.

Tartakow et al., "Urea Peroxide Solution in the Treatment of Gingivitis in Orthodontics," *Am. J. Orthod.*, vol. 73, No. 5, pp. 560–567 (May 1978).

Tassman, Gusstav et al., "Hygiene in Problem Patients," *Dental Surgery*, pp. 35–42 (Feb. 1963).

Trask, P., "Orthodontic Positioner Used for Home Fluoride Treatments", *American Journal of Orthodontics*, vol. 67, No. 6, pp. 677–682 (Jun. 1975).

Tyldesley, W.R., "Acidic Stain Removers: A Short Report", *Dental Practitioner & Dental Record*, vol. 20, No. 9, May 1970, pp. 311–313.

Ward, Marcus L., "The Americna Textbook of Operative Dentistry," pp. 491–497 (1920).

Warren, K., "Bleaching Discolored Endodontically Treated Teeth" *Restorative Dent.*, vol. 1, No. 5, Jul. 1985.

Wayman, Blake E. et al., "Vital Bleaching Technique For Treatment of Endemic Fluorosis", *General Dentistry*, Sep.–Oct. 1981, pp. 424–427.

Weisz, W.S., "Reduction of Dental Caries Through the Use of a Sodium Fluoride Mouthwash," *The Journal of the American Dental Association*, pp. 454–455, vol. 60 (Apr. 1960).

Yarborough, David K., "Tooth Bleaching Safety and Efficacy—A Review of the Literature 1988–1990," pp. 1–16.

Younger, Harold B., "Bleaching Mottled Enamel", *Texas Dental Journal*, vol. 60, No. 12, Dec. 1942, pp. 467–469.

ZIllich, Richard M., "Bleaching Tetracycline Stains," *The Compendium of Continuing Education*, vol. V, NO. 6, pp. 465–470 (Jun. 1984).

"A New Look For Your Smile", *JADA Guide to Dental Health*, Special Issue, 1987, pp. 55–59.

Adept Report, vol. 2, No. 1 (Winter 1991) entitled "Lightening Natural Teeth."

Den–Mat Corporation advertisement for "Rembrant Lighten Bleaching Gel" in *Dental Products Report*, p. 97 (Feb. 1990).

*Lexikon der dentalen Technologie—Dental Technology Dictionary*, Quintessenz Verlags—GmbH, pp. 274 275, 350, 351 (1986).

Hackh's Chemical Dictionary, p. 440, McGraw Hill (4th Ed. 1969).

M & M Innovations advertisements for "Nu–Smile" dental bleaching system originally appearing in *Dental Products Report* (Nov. 1989).

"Die Wichtmetalle in der Zahntechnik," *Grundwissen für Zahntechniker Werkstoffkunde*, Band II, Caesar/Ernest (Erste Auflage)—Non Metals in Dental Technology, *basic Sciences for Dental Technicians Materials Science*, vol. II, 1987 Caesar/Ernest (1st ed.).

Omnii International Advertisement for White & Brite (to the best of Applicant's knowledge and belief, this reference was published at least as early as Mar. 21, 1990).

Omnii International Advertisement for Fluorides, etc. (to the best of Applicant's knowledge and belief, this reference was published at least as early as Mar. 21, 1990).

Physician's Desk Reference, 1168, 1584, published by Medical Economics Co., Inc., Oracle, No., NJ., (38th Ed. 1984).

Product Insert, for Peroxgel™ Oral Antiseptic & Cleanser, Lot No. 55008, Product Code NDC 0021–0150–12, Product Insert No. 4210220044.

Remington's Pharmaceutical Sciences, 1256, Mack Publishing (16th Ed. 1980).

Research on Whitening Teeth Makes News, *The North Carolina Dental Review* vol. 7, No. 2, Fall 1990.

T & S Dental and Plastics Co., Inc. "Instruction Manual for the Machine Precision Vacuum Adapter," pp. 1–20 (to the best of Applicant's knowledge and belief, this reference was published at least as early as Mar. 21, 1990).

"The Third Stage of Comprehensive Treatment: Finishing", p. 451 (1986).

"Tooth Bleaching, Home Use Products," *Clinical Research Associates Newsletter*, vol. 13, Issue 7, (Jul. 1989).

"Tooth Bleaching, Home–Use Products," *Clinical Research Associates Newsletter*, vol. 13, Issue 12, (Dec. 1989).

Deposition of Dr. Thomas Marvin Austin with Exhibits, Civil Action No. 91–1406 W (Sx) (C.D. Cal.) (Aug. 1991).

Declaration of P. Michael Clinard, Civil Action No. 91–1406 W (Sx) (C.D. Cal.) (Sep. 1991).

Deposition (Group) of Coastal Dental Study Club, Civial Action No. 91–1406 W (Sx) (C.D. Cal.) (Sep. 1991).

Declaration of Dr. David H. Freshwater (2), Civil Action No. 91–1406 W (Sx) (C.D. Cal.) (Jul. 1991).

Deposition of Dr. David H. Freshwater with Exhibits, Civil Action No. 91–1406 W (Sx) (C.D. Cal.) (Sep. 1991).

Deposition of Dr. Van B. Haywood with Exhibits, Civil Action No. 91–1406 W (Sx) (C.D. Cal.) (Sep. 1991).

Declaration of Dr. William W. Klusmeier (2), Civil Action No. 91–1406 W (Sx) (C.D. Cal.) (Apr. 1991).

Deposition of Dr. William Walter Klusmeier, Jr. with Exhibits, Civil Action No. 91–1406 W (Sx) (C.D. Cal.) (Apr. 1991).

Deposition of Dan Parker with Exhibits, Civil Action No. 91–1406 W (Sx) (C.D. Cal.) (Aug. 1991).

Declaration of Paula Rains, Civil Action No. 91–1406 W (Sx) (C.D. Cal.) (May 1991).

Declaration of Dr. Phil S. Sanders, Civil Action No. 91–1406 W (Sx) (C.D. Cal.) (Jul. 1991).

Deposition of Dr. Phil S. Sanders with Exhibits, Civil Action No. 91–1406 W (Sx) (C.D. Cal.) (Jul. 1991).

Declaration of Dr. Jerry Wagner, Civil Action No. 91–1406 W (Sx) (C.D. Cal.) (May 1991).

Deposition of Dr. Jerry Wagner, Civil Action No. 91–1406 W (Sx) (C.D. Cal.) (Aug. 1991).

Deposition of Harry F. Albers, Civil Action No. 2:95CV 0163W (D. Utah) (Feb. 1996).

Deposition of Dr. Van B. Haywood, Civil Action No. 2:95CV 0163W (D. Utah) (Jan. 1996).

Expert Report of Dr. Van B. Haywood, Civil Action No. 2:95CV 0163W (D. Utah) (Jan. 1996).

Trial Testimony of Harry F. Albers (Direct), Civil Action No. 2:95CV 0163W (D. Utah) (May 1996).

Trial Testimony of Dan E. Fischer (Direct and Rebuttal), Civil Action No. 2:95CV 0163W (D. Utah) (May 1996).

Trial Testimony of Roger Hicks (Rebuttal), Civil Action No. 2:95CV 0163W (D. Utah) (May 1996).

Trial Testimony of Byran D. Tarr (Direct), Civil Action No. 2:95CV 0163W (D. Utah) (May 1996).

Trial Testimony of Garold S. Yost (Rebuttal), Civil Action No. 2:95CV 0163W (D. Utah) (May 1996).

Trial Testimony of Wayne Smith Gundry (Direct), Civil Action No. 2:95CV 0163W (D. Utah) (May 1996).

Trial Testimony of Walter O. Dixon (Direct), Civil Action No. 2:95CV 0163W (D. Utah) (May 1996).

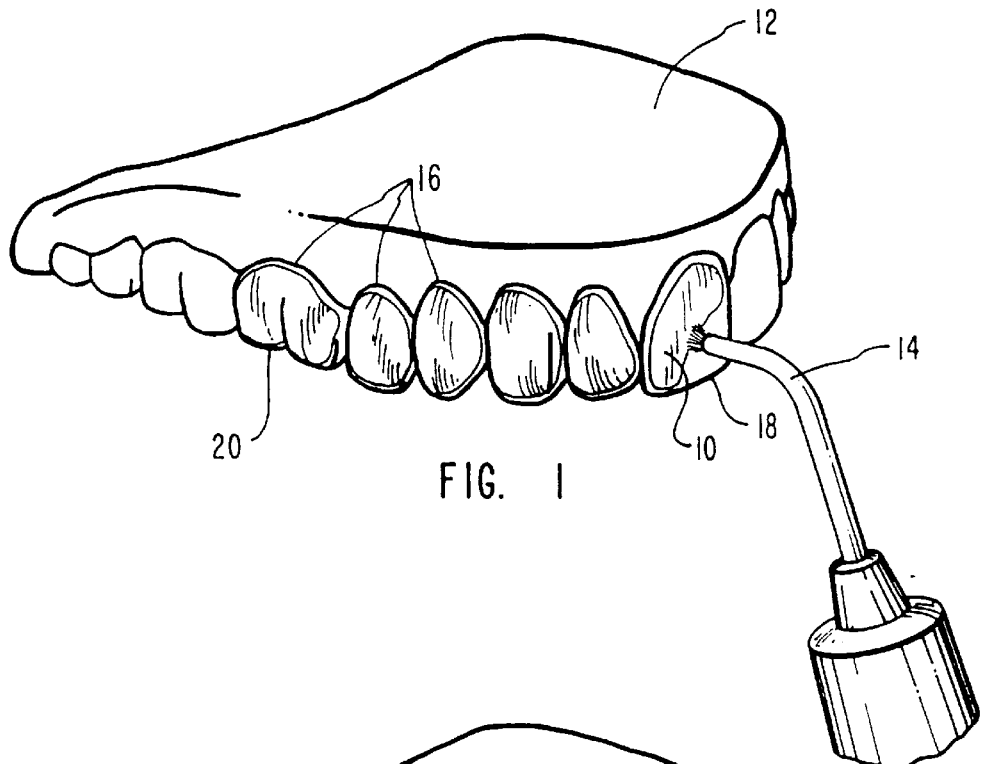
FIG. 1
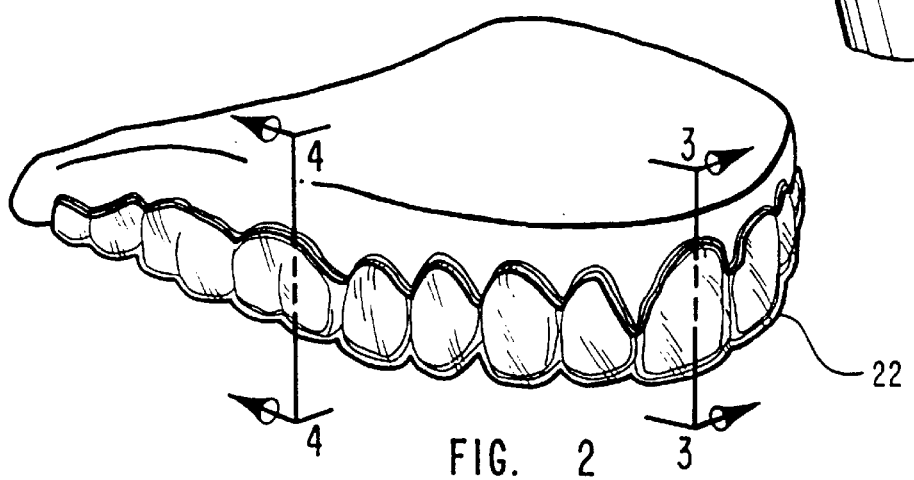
FIG. 2
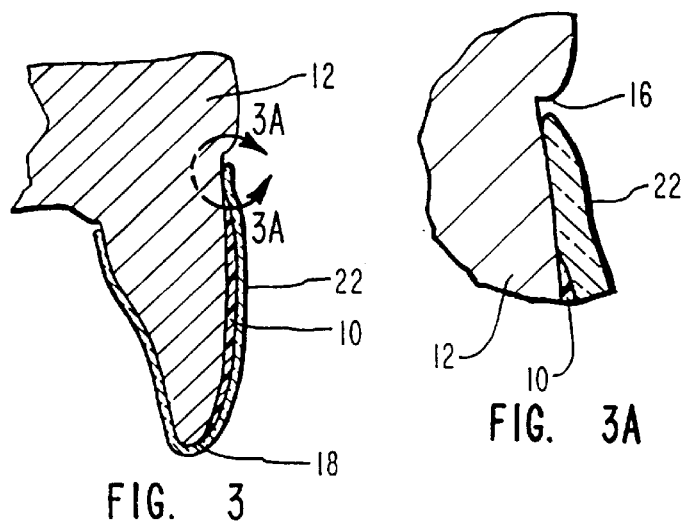
FIG. 3
FIG. 3A

STICKY DENTAL COMPOSITIONS FOR ADHERING A PASSIVE-TYPE DENTAL TRAY OVER A PERSON'S TEETH

1. Related Applications

This application is a continuation-in-part of U.S. application Ser. No. 08/865,910, filed May 30, 1997, U.S. Pat. No. 5,851,512, and also a continuation-in-part of copending U.S. application Ser. No. 08/722,549, filed Sep. 27, 1996, U.S. Pat. No. 5,725,843, which is a continuation of copending U.S. application Ser. No. 08/378,315, filed Jan. 25, 1995, U.S. Pat. No. 5,770,182, which is a continuation of U.S. application Ser. No. 08/099,247, filed Jul. 28, 1993, abandoned, which is a continuation of U.S. application Ser. No. 07/985,700, filed Dec. 2, 1992, abandoned, which is a continuation of U.S. application Ser. No. 07/718,210, filed Jun. 20, 1991, abandoned, which is a division of U.S. application Ser. No. 07/497,934, filed Mar. 22, 1990, abandoned. For purposes of disclosing the present invention, the foregoing patents and applications are incorporated herein by specific reference.

BACKGROUND

2. The Field of the Invention

The present invention relates to sticky dental compositions used in treating a person's teeth and gums. More particularly, the present invention is directed to sticky matrix materials into which a variety of different dental agents and/or agents for treating gums can be dispersed. The novel compositions are preferably used in combination with a thin-walled, comfortable fitting dental tray in order to provide prolonged treatment of a patient's teeth and/or gums for a desired period of time.

3. The Relevant Technology

Most people have experienced a variety of tooth and/or gum ailments at sometime in their lives. In addition, some have sought to cosmetically enhance the appearance of their teeth through bleaching. Bleaching compositions typically include a bleaching agent such as hydrogen peroxide or carbamide peroxide dispersed within a low viscosity carrier.

Other medicaments for treating teeth and gums include desensitizing agents for treating painful or sensitive teeth, anticariogenic agents for treating or preventing the formation of cavities, and antimicrobial agents used to fight dental and gum diseases.

The foregoing compositions are typically applied directly to a person's teeth. In some cases, such as in the case of dental bleaching compositions, such compositions can be loaded within a dental tray.

Conventional dental trays, including those specifically adapted for delivering a medicament to a person's teeth, as well as mouthguards used to protect a person's teeth while playing sports, remain in place by means of mechanical pressure exerted by the dental tray onto the person's teeth. Unfortunately, the exertion of mechanical pressure onto a person's teeth can create significant discomfort and cause a disincentive for continuing a tooth treatment regimen.

For example, dental trays such as those described in U.S. Pat. No. Re 34,196 to Munro are adapted to be held in place by mechanical fit and provide a liquid-tight seal over the person's gums in order to for the tray to retain a generally non-viscus bleaching composition against a person's teeth. Like dental trays that exert mechanical pressure onto a person's teeth, dental trays such as those disclosed in Munro, which are specifically designed to be self-retaining such that they will remain in place due to mechanical fit by creating a liquid-tight seal about a person's gums, can result in significant discomfort and result in diminished desire to complete a dental treatment regimen.

As set forth in the parent applications identified above, e.g., U.S. application Ser. No. 07/497,934, the inventor has developed flexible, thin-walled dental trays that exert little or no significant mechanical pressure on a person's teeth when in place to provide a more comfortable fit. The inventive dental trays optionally include reservoirs for providing more of a dental composition against one or more of the person's teeth. Furthermore, the dental tray can alternatively be configured to overlap a portion of the person's gums or it may be trimmed at or below the gingival margin in order to maintain the dental composition away from the person's gums. In either scenario, the inventive dental trays exert little or no significant mechanical pressure onto the person's teeth or gums so that the trays are more pleasant to use.

Unfortunately, since the comfortable dental trays exert little or no significant mechanical pressure onto a person's teeth or gums, the dental trays may not reliably remain in place over, or otherwise be dislodged from a person's teeth, thereby interrupting or disturbing the treatment regimen. Conventional dental compositions used with tight fitting trays which provide their own mechanical gripping mechanism are not intended for use with the inventive, comfortable fitting, thin-walled trays set forth and, e.g., U.S. application Ser. No. 07/497,934. Hence, such dental compositions have not heretofore been formulated with the necessary adhesive action. Similarly, since desensitizing agents used in dental office are non-sticky, nonviscous fluids while toothpaste can include other dental agents, are not adapted for use with dental trays, there has not heretofore existed a dental composition for treating teeth and gums that could be used in conjunction with the comfortable fitting dental trays developed by the inventor.

It would be an improvement in the art to provide compositions for treating teeth and/or gums that were sufficiently sticky and resistant to dilution by saliva such that they had the ability to adhere and retain a flexible, thin-walled dental tray in place against a person's teeth, wherein the dental tray did not exert significant mechanical pressures onto the person's teeth or gums and was not designed to stay in place over a person's teeth due to mechanical fit.

It would be a further improvement in the art to provide sticky dental compositions that allowed for more secure and reliable contact between the active dental agent and a person's teeth and/or gums in order to provide more reliable and complete treatment of a person's teeth and/or gums.

Additionally, it would be a significant advancement in the art to provide dental compositions for treating teeth that could be adapted for use by disabled or semi-debilitated people who may not have the strength, coordination or ability to brush their teeth without the assistance of others.

It would be a tremendous advancement in the art if such dental compositions included a sticky matrix material that could be used in conjunction with a variety of dental agents for providing a variety of different treatments of a person's teeth and/or gums.

Such compositions including a sticky matrix for treating a person's teeth are disclosed and claimed herein.

BRIEF SUMMARY AND OBJECTS OF THE INVENTION

The present invention is directed to sticky dental compositions that may include a variety of different medicaments or dental agents for a number of different teeth and/or gum ailments. The dental compositions include a sticky matrix material into which an appropriate dental agent is dispersed. An improved dental tray that is preferably thin-walled, flexible and lightweight is preferably used to hold the dental composition adjacent to the person's tooth surfaces to be treated. The preferred dental tray should be adapted for maximum comfort and will exert little if any significant mechanical pressure onto the person's teeth or gums and will not be designed to stay in place over a person's teeth due to mechanical fit. Accordingly, the improved dental compositions should be sufficiently sticky and resistant to dilation by saliva such that they can act as a glue and reliably adhere and retain the dental tray over the person's teeth for varying time durations.

The appropriate dental agent is preferably dispersed within a sticky, glue-like matrix material to form the sticky dental composition. Suitable sticky matrix materials are preferably safe for oral use, do not readily dissolve in saliva, and do not react with the dental agent being employed. One currently preferred sticky matrix material includes carboxypolymethylene together with other suitable admixtures. The term "carboxypolymethylene" is used to denote a broad category of polymers, particularly copolymers of acrylic acid and polyallyl sucrose. Because carboxypolymethylene includes carboxylic acid groups or moieties, it can be classified as a weak acid. When dispersed in water, carboxypolymethylene can have a pH as low as about 2.5.

Although water is only optionally included within the compositions of the present invention, since a person's mouth includes saliva, which is aqueous, it would generally be detrimental to a person's teeth to apply a composition that can become acidic in the presence of saliva, since acids can attack tooth enamel. Accordingly, it is preferable to adjust the pH of compositions that include carboxypolymethylene with a range from about 4 to about 9, more preferably in a range from about 5 to about 7. Because it is contemplated that the carboxypolymethylene used in the matrix material and the compositions of the present invention will be neutralized to a certain extent, the term "carboxypolymethylene" shall include carboxypolymethylene polymers at any pH, whether in a neutralized, partially neutralized, or non-neutralized form.

The matrix material can include other optional components in addition to the carboxypolymethylene in order to provide bulk and also to yield a matrix material having the desired level of stickiness. One such admixture is glycerin, which is easily mixed with carboxypolymethylene. Another optional component is water, as set forth above. It is preferable to use a base in order to adjust the pH of the matrix material. Preferred bases can include inorganic bases such as sodium hydroxide or ammonium hydroxide. Alternatively, the base may include an organic base such as triethanolarnine or other organic anines. Other admixtures that can improve the adhesiveness and rheological properties of the matrix material include cellulosic ethers, polysaccharide gums (e.g., xanthan gum) and polyols.

Because the compositions of the present invention can be adapted to treat a variety of tooth and/or gum ailments, one can select an appropriate dental agent to be dispersed within the inventive sticky matrix material. One such dental agent includes a bleaching agent such as carbamide peroxide or hydrogen peroxide. It is believed that upon decomposing, the oxygen radicals emitted by the decomposing peroxide ions are able to permeate into the micropores of a person's teeth in order to provide bleaching of the tooth enamel. Because of this, the more reliable adhesion provided by the sticky matrices of the present invention and the ability of the sticky dental compositions to adhere and retain a comfortable fitting thin-walled dental tray against a person's teeth greatly improves the chances of successful bleaching of a person's teeth.

In order for the sticky dental compositions to provide relief for painful or sensitive teeth, a desensitizing agent can be dispersed within the sticky matrix material. Examples of preferred desensitizing agents within the scope of the present invention include potassium nitrate ($KNO_3$), citric acid, citric acid salts, strontium chloride, and the like. Since desensitizing agents must penetrate into the pores of a person's teeth in order to reach the nerves within the dental pulp, the sticky compositions of the present invention allow for prolonged contact between the dental agent and the person's teeth.

Other dental agents can be added or substituted for the bleaching agent or desensitizing agent to provide other useful properties or activities to the dental compositions. For example, fluoride salts can be added in order to add an anticariogenic property to the tooth desensitizing compositions. Peroxides can also be added in order to provide a disinfecting action. Since peroxides are known to cause irritation and also greater sensitivity in teeth, the simultaneous inclusion of a desensitizing agent can offset the negative effects of the peroxide.

Examples of preferred antimicrobial agents that can be added to fight gum and periodontal diseases include chlorhexadine, tetracycline, cetyl pyridinium chloride, benzalkonium chloride, cetyl pyridinium bromide, methyl benzoate, and propyl benzoate.

The sticky dental compositions within the scope of the present invention are sufficiently sticky and generally viscous such that positive pressure is needed to dispense them from the container; gravity is not sufficient. Unlike conventional low-viscosity compositions such as GLY-OXIDE (manufactured by Marion Laboratories) or PROXIGEL (manufactured by Reed and Carnick according to U.S. Pat. No. 3,657,413 to Rosenthal), the sticky dental compositions of the present invention cannot be dispensed drop-wise from a bottle. A syringe, squeezable tube, or other similar positive pressure dispensing device is needed to dispense the dental compositions within the scope of the present invention.

An improved dental tray that is thin-walled, flexible and lightweight for holding the dental composition adjacent to a person's teeth is preferably used in combination with the sticky dental compositions of the present invention. The general process for preparing such dental trays is as follows. First, an alginate impression which registers all teeth surfaces plus the gingival margin is made and a stone cast is made of the impression. Optional reservoirs can be prepared by building a layer of a solid material on the stone cast on specific teeth surfaces to be treated. Such blockout materials might include polymerizable materials, wax, modeling clay, or any other plastic and/or higher melting point material that can be used to coat a stone case for forming reservoirs.

A dental tray is then vacuum formed from the modified cast using a thin, flexible membrane material. Once formed, the tray is preferably trimmed barely shy of the gingival margin on both the buccal and lingual surfaces of the person's teeth. The resulting tray provides a custom fit of the person's teeth with optional reservoirs or spaces located where the blockout material was placed on the stone cast. The trays can optionally overlap the gums if desired to provide contact between the dental compositions and a person's gums. The trays of the present invention have greatly increased comfort and exert little or no significant mechanical pressure on a person's teeth or gums. Instead, the sticky dental compositions act like a glue to hold the inventive trays in place.

The level of clinical benefit that may be obtained by using the inventive dental compositions is dependent upon (1) the length of time each day the tray is worn; (2) the number of days the tray is worn; and (3) the susceptibility of the teeth to the dental agent in question. The treatment schedule may be tailored to each person's lifestyle or response to the treatment and can be performed as often as a person desires to provide effective relief from a variety of tooth and/or gum ailments. It has been found that treatment during sleep is a good treatment time of the day since less mouth activity will pump the dental composition from the tray.

Accordingly, it is an object of the present invention to provide compositions for treating teeth and/or gums that are sufficiently sticky and resistant to dilution by saliva such that they have the ability to adhere and retain a flexible, thin-walled dental tray in place against a person's teeth, wherein the dental tray does not exert significant mechanical pressures onto the person's teeth or gums and is not designed to stay in place over a person's teeth due to mechanical fit.

It is a further object of the present invention to provide sticky dental compositions that allow more secure and reliable contact between the active dental agent and a person's teeth and/or gums in order to provide more reliable more reliable and complete treatment of the person's teeth and/or gums.

It is an additional object and feature of the present invention to provide dental compositions for treating teeth that can be adapted for use by disabled or semi-debilitated people who may not have the strength coordination or ability to brush their teeth without the assistance of others.

It is yet another object of the invention to provide dental compositions that include a sticky matrix material that can be used in conjunction with a variety of dental agents for providing a variety of different treatments of a person's teeth and/or gums.

These and other objects and features of the present invention will become more fully apparent from the description as follows, or may be learned by the practice of the invention.

BRIEF DESCRIPTION OF THE DRAWINGS

FIG. 1 is a perspective view of a stone cast of a patient's teeth with a rigid coating being applied to selected teeth surfaces.

FIG. 2 is a perspective view of the stone cast of FIG. 1 with a dental tray formed from the cast and trimmed below the gingival margin.

FIG. 3 is a cross-sectional view taken along line 3—3 of FIG. 2.

FIG. 3A is an enlarged close-up view taken within the section line 3A—3A of FIG. 3.

DETAILED DESCRIPTION OF THE PREFERRED EMBODIMENTS

Figure 4:
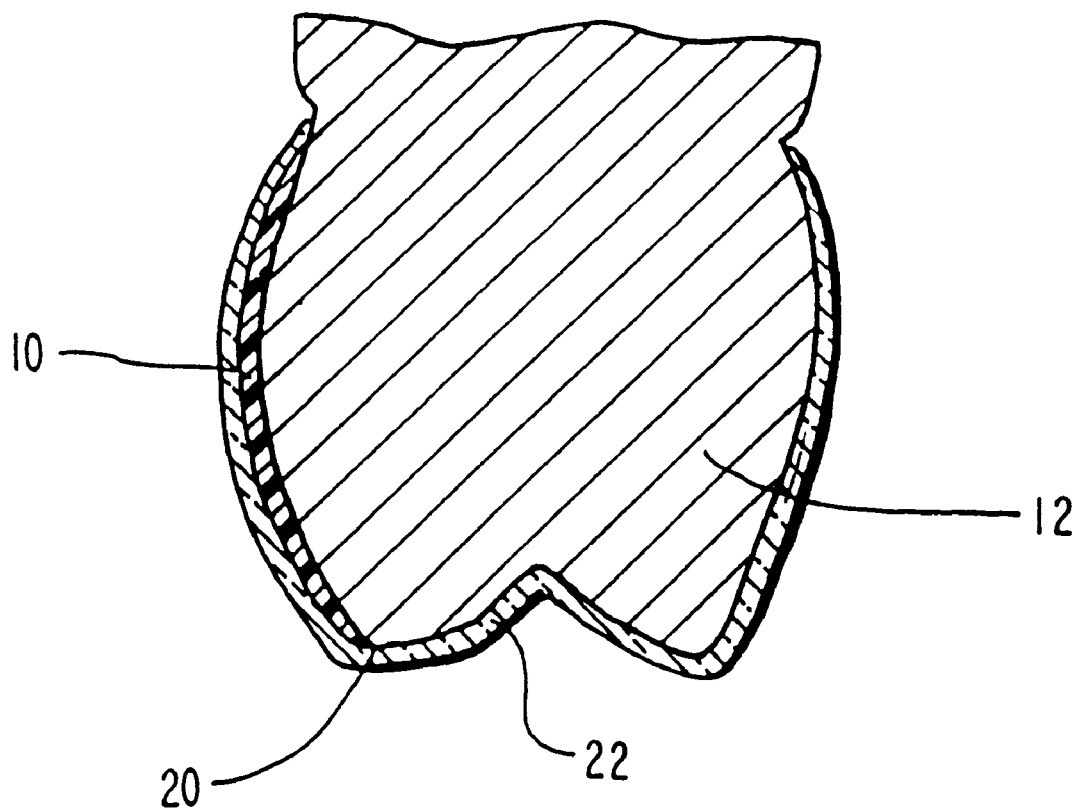
FIG. 4 is a cross-sectional view taken along line 4—4 of FIG. 2.

As summarized above, the present invention generally relates to sticky, glue-like dental compositions used in treating a variety of different tooth and/or gum ailments. Such compositions are preferably used in conjunction with, and to adhere in a glue-like fashion, improved dental trays that are preferably thin-walled, flexible, and lightweight. Such trays exert little or no significant mechanical pressure onto the person's teeth and/or gums, which makes them more comfortable and pleasant to use compared to other dental trays. It is the glue-like action of the sticky dental compositions of the present invention that adheres and retains the tray over a person's teeth. Prior dental treatments that employed a dental tray have employed lower viscosity, non-sticky liquids that rely on the mechanical pressure and fit of the tray to hold and retain the tray against the person's teeth.

The inventive dental compositions include one or more dental agents that are dispersed within a sticky matrix material. Suitable sticky matrix materials are preferably safe for oral use, do not readily dissolve in saliva, and do not react with or inactivate the dental agent being used. One currently preferred sticky matrix material includes carboxypolymethylene together with other suitable admixtures. Carboxypolymethylene is a broad term that refers to vinyl polymers having active carboxyl groups. Suitable carboxypolymethylene compositions may be obtained from B. F. Goodrich Company under the tradename "CARBOPOL". Another tradename for carboxypolymethylene is CARBOMER. In its non-neutralized form, carboxypolymethylene can have a pH as low as 2.5. As discussed below, the pH of carboxypolymethylene can be raised to yield carboxypolymethylene in a neutralized or partially neutralized state.

The amount of carboxypolymethylene within the inventive dental compositions can vary depending on the desired level of stickiness and also the identities and amounts of the other components within the dental composition. With the understanding that it is the concept of stickiness or adhesive ability that is the important feature of the compositions of the present invention, one of ordinary skill in the art can alter the concentrations of the various components to yield dental compositions that are able to exert an adhesive force sufficient to reliably adhere and maintain a dental tray against a person's teeth without significant mechanical pressure being exerted by the dental tray. In general, the dental compositions of the present invention will preferably include carboxypolymethylene in a concentration in a range from about 0.5% to about 20% by weight of the dental composition, more preferably in a range from about 2% to about 12% and most preferably in a range from about 3% to about 10%.

It should be understood that the actual amount of carboxypolymethylene is not critical. The important thing is that the composition have the required amount of stickiness and adhesive ability. The matrix material may include other tackifying and rheology-modifying components that in combination with, or in lieu of some or all of, the carboxypolymethylene will yield a dental composition having the desired level of stickiness needed to hold a dental tray in place over a person's teeth. Other synthetic polymers and/or adjuvants, such as natural gums, proteins, cellulosic ethers, high molecular weight polyols, or other gel-forming admixtures, can be used so long as they yield a sticky dental composition.

One currently preferred carboxypolymethylene resin is known by the tradename CARBOPOL 934P. CARBOPOL 934P is a high purity pharmaceutical grade of CARBOPOL 934, having an approximate molecular weight of about 3,000,000. In addition to thickening, suspending, and emulsifying, CARBOPOL 934P has been used in dry tablets to impart sustained release properties. Extensive toxicity studies have been conducted on CARBOPOL 934P, and a master file has been established with the Food and Drug Administration. It is listed as CARBOMER 934P in the National Formulary. A more recently preferred carboxypolymethylene is CARBOPOL 974P NF, which has more recently surpassed CARBOPOL 934P as the carboxypolymethylene of choice. Although CARBOPOL 974P NF is similar or identical in molecular weight compared to CARBOPOL 934P, it is purified in a way that makes it more pharmaceutically acceptable material.

It is believed that other carboxypolymethylene resins, such as CARBOPOL 940, may be substituted for CARBOPOL 934P or CARBOPOL 974P NF. In addition, CARBOPOL 934P and CARBOPOL 974P NF are currently preferred because they are obtainable in a pharmaceutical grade. It was the inventor that first discovered that carboxypolymethylene can be used to form a glue-like dental composition that can be used as an adhesive to hold a passive-type dental tray against a person's teeth, which has eliminated the need to use dental trays that are self-retaining, ie., which are designed exert enough mechanical pressure onto a person's teeth and/or gums such that they will be reliably retained in place over a person's teeth for a desired period of time due to mechanical fit. In order to reliably hold and retain the thin-walled dental trays of the present invention over a person's teeth, the sticky dental compositions should have a stickiness and resistance to dilution to saliva such that they can retain and hold a dental tray that is not designed to stay in place over the teeth due to mechanical fit for at least about one hour without significant mechanical force exerted by the tray, more preferably at least about two hours, and most preferably at least about three hours.

The sticky dental compositions within the scope of the present invention have a number of important characteristics in addition to stickiness and high viscosity. They are also resistant to dilution by saliva such that a significant quantity of saliva or water is required to lower the viscosity to the point that the dental composition may be diluted and washed out by salivating action. Because the carboxypolymethylene reduces the risk of dilution from saliva and increases the time for salivary dilution, the resulting dental compositions are able to provide prolonged exposure of the teeth to the dental agent within the dental composition. In addition, the stickiness of the compositions ensures good contact between the composition and the person's teeth.

In order to obtain good dispersion of the carboxypolymethylene resin within the dental composition, it is recommended that the carboxypolymethylene be mixed with a quantity of glycerine, other polyol, or like substance before attempting to add other components that are less compatible with carboxypolymethylene, such as water. Glycerine and other polyols appear to enable larger quantities of carboxypolymethylene to be dispersed in water. It has also been observed that once the carboxypolymethylene and glycerine and/or other polyol have been mixed together, it is preferable to quickly disperse the resulting mixture in the water or else it can stiffen to the point where addition of water becomes impracticable. It is preferable that the concentration of glycerine, polyol, or like substance in the dental compositions of the present invention be in a range from about 20% to about 85% by weight of the dental compositions, more preferably in a range from about 30% to about 70% by weight.

Glycerine, other polyols, and the like are inexpensive fillers that work well in forming a sticky gel with carboxypolymethylene. Because glycerine is hydrophilic, it can act as an emulsifying agent if water is used. The glycerine also provides some flavor enhancement such that a bland, sweet flavor is perceived. A few possible substitutes for glycerine include propylene glycol, polypropylene glycols, sorbitol, polyethylene glycols, other polyols, mixtures thereof, and the like. Adding polyethylene glycol in addition to glycerine has been found to be useful as a processing aid. Ethylene glycol would also work but is disfavored since it can be toxic if ingested in large enough amounts.

Water may also be included within the compositions of the present invention, although more carboxypolymethylene must generally be added as water is added to maintain the same level of stickiness. The amount of water included within the dental compositions of the present invention is preferably in a range from about 0% to about 50% by weight of the dental composition, more preferably in a range from about 2% to about 30% by weight. It will be appreciated that the total quantity of water in the dental composition may come from different sources. For instance, some dental agents and bases, discussed below, may come as aqueous solutions.

Because carboxypolymethylene is a polycarboxylic acid, it tends to lower the pH of the resulting dental compositions significantly, down to a pH of about 2–5 in some cases. It appears, based upon clinical and in vitro testing, that dental compositions with a pH below about 5 are able to etch enamel. To avoid etching enamel, it is preferable to add a base in order to raise the pH of the inventive dental compositions to within a pH range of about 4 to about 9, more preferably to within a range from about 5 to about 7. Inorganic and organic bases may be used, with the use of concentrated aqueous sodium hydroxide (50% NaOH in water) being one currently preferred embodiment. Organic bases, such as triethanolamine or other amines can be used. The amount of base to be included will generally depend on the desired pH and the amount of carboxypolymethylene in the dental composition. Accordingly, bases will preferably be included in a range from about 0.2% to about 12% by weight of the dental composition.

The term "carboxypolymethylene" shall be understood to include carboxypolymethylene resins at any pH, whether neutralized, partially neutralized or non-neutralized. The term shall also include carboxypolymethylene resins that have reacted with, formed complexes with, or otherwise been altered in any way by other components within the dental compositions of the present invention so long as the carboxypolymethylene is able to impart the desired level of stickiness to the final dental composition in combination with the other components within the dental composition.

Preferred dental bleaching agents according to the present invention include peroxides such as hydrogen peroxide and carbamide peroxide. The amount of bleaching agent that can be included within the dental compositions of the present invention may vary according to the desired strength and intended treatment times. Accordingly, the bleaching agent will preferably be included in an amount in a range from about 3% to about 30% by weight of the dental composition, more preferably in a range from 4% to about 20% by weight. Other bleaching agents are certainly within the scope of the present invention and their concentration can be adjusted by those of ordinary skill in the art to provide appropriate bleaching strength. Sticky dental compositions of the present invention ensure good contact between the bleaching agent and a person's teeth for extended periods of time.

Preferred tooth desensitizing agents that can be used with the inventive sticky matrix materials include potassium nitrate, citric acid, citric acid salts, strontium chloride, and the like. The amount of desensitizing agent that can be included within the dental compositions of the present invention may vary according to the desired strength and intended treatment times. Accordingly, the desensitizing agent will preferably be included in an amount in a range from about 0.1% to about 10% by weight of the dental composition, more preferably in a range from about 1% to about 7% by weight. Other desensitizing agents are certainly within the scope of the present invention and their concentration can be adjusted by those of ordinary skill in the art to provide appropriate relief from sensitive teeth. The sticky dental compositions of the present invention can ensure good contact between the desensitizing agent and a person's teeth for extended periods of time.

Instead of or in addition to the bleaching and desensitizing agents, it may be desirable to include other active dental agents to provide other types of dental and/or gum treatment. For example, in conjunction with tooth bleaching and/or desensitization, it may be desired to provide an anticariogenic treatment. Preferred anticariogenic agents include fluoride salts, more particularly sodium monofluorophosphate, sodium fluoride, and stannous fluoride. Depending on the level of fluoride treatment desired, and depending on whether or not a composition is "over-the-counter" or "by prescription", the fluoride may preferably be included in a range from about 0% to about 1% by weight of the dental composition, more preferably in a range from about 0.1% to about 0.5% by weight.

Antimicrobial agents, e.g., for fighting gum disease, may be included within the sticky dental compositions of the present invention. Examples of useful antimicrobial agents include chlorhexadine, tetracycline, cetyl pyridinium chloride, benzalkonium chloride, cetyl pyridinium bromide, methyl benzoate, and propyl benzoate. The antimicrobial agents may preferably be included in an amount in a range from about 0.1% to about 15% by weight of the dental composition, more preferably in a range from about 0.1% to about 5% by weight.

In order to preserve the stability of the dental compositions, it is often preferable to include an ion scavenger such as EDTA, salts of EDTA, citric acid, succinic acid, and adipic acid, which are commonly-used chelating agents. Ion scavengers may preferably be included in an amount in a range from about 0% to about 1% by weight of the dental composition, more preferably in a range from about 0.01% to about 0.5% by weight.

Finally, although most peroxides such as hydrogen peroxide and carbamide peroxide have been found to be unstable in the presence of potassium nitrate, it may be possible to add peroxide to the dental compositions of the present invention shortly before treatment in order to combine the bleaching and/or antiseptic action of the peroxide with the desensitization action of the potassium nitrate. In the event that a stabilizing agent could be found that would make peroxides and potassium nitrate stable when mixed together without diminishing the effects of the potassium nitrate, such a combination certainly would be contemplated within the present invention.

Unlike existing low-viscosity compositions, such as PROXYGEL, which are placed drop-by-drop into the tray, the sticky dental compositions within the scope of the present invention have a stickiness and viscosity such that they cannot be dispensed drop-wise into a dental tray from a bottle. Positive pressure is needed to expel the dental compositions of the present invention from the container; gravity is not sufficient.

One currently preferred method of dispensing the inventive sticky dental compositions is by means of a syringe. Squeezable tubes and other similar dispensing devices may also be used to dispense the compositions. Upon dispensing, the sticky dental compositions are sufficiently viscous that they do not easily settle or spread once dispensed, but will generally remain as a single extruded strand or bead of dental composition.

It is currently preferred to provide a unit dose of the sticky dental compositions in a syringe or similar dispensing device. In this way, the person can load the precise amount of dental composition onto the dental tray for each treatment period. By using such dispensing devices, the dentist is also able to monitor how many doses the person has received and used.

Although not required, the sticky dental compositions of the present invention are preferably used to treat a person's teeth in conjunction with passive-type dental trays that exert little or no significant mechanical pressure onto a person's teeth and gums. The result is a more comfortable and pleasant feeling dental tray, unlike prior art dental trays which are generally rigid and/or thick-walled such that they exert sufficient mechanical pressures onto the teeth and/or gums to be "self-retaining". That is, prior dental trays can be used with dental compositions which are neither sticky nor viscous since the compositions are not relied upon to adhere and retain the self-retaining prior art dental trays. In contrast, preferred dental trays used according to the present invention exert little if any significant mechanical pressure onto a person's teeth and/or gums and are not designed to stay in place over the teeth due to mechanical fit.

In the general process for preparing the dental trays according to the present invention, an alginate impression is made which registers all teeth surfaces plus the gingival margin. Thereafter, a stone cast is made of the impression. Excess stone can be trimmed away for easy manipulation and forming the dental tray.

Reference is now made to FIGS. 1–4. In a preferred method for forming a dental tray, one or more reservoirs can be formed in the resultant dental tray by applying a thin coating of a blockout material 10 to the stone cast 12 corresponding to teeth where it is desired to provide more of the dental composition. As depicted in FIG. 1, the blockout material 10 may be applied using a brush tipped applicator 14. The blockout material 10 may be light curable resin for convenience. However, it can be any material that is plastic when applied but which will remain in place over the stone cast and form reservoirs within the dental tray. It can be wax, modeling clay or a high melting point material. In those instances where the dental tray is to be trimmed below the gingival margin, the coating material will preferably be applied in a manner that is kept at a distance of at least about 1 mm from the gingival line 16, more preferably in a range from about 1.25 to about 1.5 mm from the gingival line 16.

The finished coating will have a thickness corresponding to the desired reservoir depth, which will commonly be about 0.5 mm. It is generally preferred that the rigid coating material not be applied over the stone cast corresponding to the incisal edges and occlusal edges 20 of the person's teeth. This because it is preferable for the incisal edges and occlusal edges of the person's actual teeth to contact the finished tray in order to prevent or reduce vertical movement of the tray during use, which movement could act as a pump that could express the dental composition from the tray and result in the intake of saliva within the dental tray.

A dental tray 22 is then vacuum formed from the stone cast using conventional techniques. The dental tray 22 is preferably constructed of a soft vinyl or vinyl-like material preferably having a preformed thickness in a range from about 0.5 mm to about 3 mm, more preferably in a range from about 1 mm to about 2 mm. Soft materials yield dental trays that are more comfortable for the patient to wear. It will be appreciated that the final tray thickness may vary depending on the technique used to prepare the tray, as well as the size and shape of the person's teeth. Patients suspected of being breuxers or hard biters may require either a thicker or a harder material. Of course, patients should be counselled not to eat with trays in place or to bite firmly into them.

In those cases where the dental composition will be used to treat a person's teeth only, the dental tray 22 is preferably trimmed barely shy of the gingival margin 16 of the person's teeth on both the buccal and lingual surfaces for maximum comfort. Enough tray material should be left to assure that the teeth will preferably be covered to within about ¼ mm to about ⅓ mm of the gingival border upon finishing and beveling of the tray periphery. It is also generally preferred to scallop up and around the interdental papilla so that the finished tray does not cover them. The tray edges are preferably smoothed so that the lip and tongue will not feel an edge prominence. Slight adjustments to the tray may be made by carefully heating and stretching the tray material. The foregoing description is illustrative and not limiting.

From practice, it has been found that patients may experience less tooth discomfort from tray pressures when using a tray with reservoirs built into the tray as described above. It is currently believed this is due to the fact that the teeth are not held as firmly by the tray, so that "orthodontic" pressures experienced by teeth from tray discrepancies are minimized. The use of thin, soft tray materials further minimizes these "orthodontic" forces, compared to the harder plastics currently used in the art, such as those described in U.S. Pat. No. Re 34,196 to Munro. Reservoirs, of course, provide more of the dental composition to the person's teeth corresponding to the reservoirs.

Although the aforementioned thin, flexible dental trays are preferred when treating a person's teeth, it may be preferable in some cases to allow the dental tray to overlap the person's gums, such as in the case where dental agents are included to fight gum diseases. Of course, to the extent that the dental compositions do not irritate the gums, the dental trays can always be constructed to overlap the gums. However, the tray should be configured so as to not exert significant mechanical pressure onto a person's gums so as to maximize comfort and compliance. Thus, overlap of the gums is not for tray-retention, as in U.S. Pat. No. Re 34,196 to Munro.

Nevertheless, it has been found that where it is desired to treat a person's teeth rather than the gums, it is generally more comfortable for the person if the dental tray has been trimmed to or below the gingival margin. Even in those cases where the dental trays will overlap the person's gums, the dental trays of the present invention preferably will not exert significant mechanical pressure onto the person's gums. Contrast this with the prior dental trays according to Munro, which specifically teach the formation of a "liquid-type seal" between the rigid dental trays and the person's gums. The purpose for this, of course, is that Munro expressly teaches the use of PROXIGEL, which is not sufficiently sticky to reliably retain and hold a dental tray that exerts no significant mechanical pressure against a person's teeth and/or gums for long durations.

Because the dental trays made according to the present invention exert little or no mechanical pressure onto a person's teeth and gums and are not designed to stay in place over a person's teeth due to mechanical fit, it is important that the inventive dental compositions be able to act a glue to reliably adhere and retain the dental tray over a person's teeth for the desired length of treatment. Accordingly, the dental compositions will preferably have a stickiness such that they can reliable adhere and retain a dental tray over a person's teeth for at least about one hour without significant mechanical pressure from the dental tray, more preferably for at least about two hours, and most preferably for at least about four hours. Nevertheless, while the foregoing time durations are given in order to provide an accurate measurement of the stickiness of the dental compositions of the present invention, they should not be taken to be a limitation as to the actual length of time that the patient may wish to use the inventive dental compositions. While a given dental composition may be able to retain the dental tray against a person's teeth for, e.g., 10 hours or more, that composition could certainly be used for 15 minutes, one hour, or for any desired time duration.

Although the use of flexible, thin-walled dental trays is certainly preferred, it is within the scope of the present invention to use the inventive sticky dental compositions with conventional trays. The increased adhesive action of the inventive dental compositions will ensure a more reliable mechanical and chemical contact between the active dental agents and the person's teeth regardless of the type of dental tray that is used. Nevertheless, it is preferable to use the inventive dental trays since they are clearly more comfortable to use compared to prior dental trays that are designed to mechanically lock themselves over a person's teeth and/or gums such that they will themselves be able to hold any type of dental composition against a person's teeth regardless of the level of stickiness, or lack thereof, of the dental composition being used.

The sticky dental compositions of the present invention may be used at any appropriate time and duration by a person in order to treat a variety of ailments. Although the sticky dental compositions of the present invention facilitate the use of flexible, thin-walled dental trays that are more comfortable to use compared to prior dental trays, the insertion of any dental tray within a person's mouth will cause some alteration of behavior and diminution of the freedom to use one's mouth. Therefore, in order to maximize treatment time and reduce the inconvenience of having a dental tray lodged within a person's mouth, it is recommended to use the dental trays at night during a person's sleep. The versatility and comfort of the disclosed treatment regimens allows for use by a person whenever convenient.

Typical treatment times for night use will range from between about 5 to 10 hours depending on the length a person remains in bed. For day use, the sticky dental compositions of the present invention have been found to provide some relief or benefit for treatment times as little as about 15 minutes, although treatment times of one to three hours are recommended.

Regardless of which treatment schedule is used, the use of the sticky dental compositions within the scope of the present invention provides a more constant level of desensitizing activity compared to home-use compositions, such as toothpaste or non-viscous compositions used with conventional tight-fitting dental trays. Since the amount and length of time the active desensitizing agent is adjacent the teeth significantly influences the efficiency of the treatment, the sticky dental compositions of the present invention represent a significant improvement over existing home-use dental systems.

In order to more clearly illustrate the parameters of the inventive dental compositions within the scope of the present invention, the following examples are presented. The following examples are intended to be exemplary and should not be viewed as limiting to the scope of the invention.

EXAMPLE 1

A sticky tooth desensitizing dental composition within the scope of the present invention was prepared by combining the following ingredients in the following proportions:

| Water | 20% |
|---|---|
| $KNO_3$ | 2% |
| CARBOPOL 974P NF | 4% |
| Sodium hydroxide (50%) | 3% |
| Disodium EDTA | 0.1% |
| NaF | 0.11% |
| Glycerine | 68.4% |

The CARBOPOL 974P NF was obtained from B. F. Goodrich Company in Cleveland, Ohio. The CARBOPOL 974P NP was first combined with the glycerine and then mixed with the water. The glycerine enabled the CARBOPOL 974P NF to be more easily mixed with the water. The $KNO_3$ and disodium EDTA were added to the mixture, after which the sodium hydroxide was blended into the homogeneous composition in order to raise the pH to an acceptable level. The resulting dental composition had both desensitizing and anticariogenic properties, and was sufficiently sticky that it could reliably hold and maintain a dental tray against a person's teeth without significant mechanical pressure being exerted by the tray onto a person's teeth and gums.

EXAMPLE 2

A sticky desensitizing dental composition within the scope of the present invention was made according to the procedure of Example 1, except that the water was excluded such that the remaining components were combined in the following amounts:

| $KNO_3$ | 2% |
|---|---|
| CARBOPOL 974P NF | 2.5% |
| Disodium EDTA | 0.1% |
| Sodium fluoride (NaF) | 0.11% |
| Sodium hydroxide (50%) | 5.4% |
| Glycerine | 89.9% |

The foregoing procedure resulted in a sticky dental composition. The resulting dental composition had both desensitizing and anticariogenic properties, and was sufficiently sticky that it could reliably hold and maintain a dental tray against a person's teeth without significant mechanical pressure on the patient's teeth and gums.

EXAMPLE 3

A dental composition within the scope of the present invention is made according to the procedure of Example 1, except that the ingredients are combined in the following concentrations by weight %:

| $KNO_3$ | 0.5% |
|---|---|
| Water | 20 |
| Glycerine | 63.6% |
| CARBOPOL 974P NF | 7% |
| Sodium hydroxide (50%) | 9.4% |

The foregoing procedure results in a sticky dental composition having reduced but significant desensitizing activity.

EXAMPLE 4

A dental composition within the scope of the present invention is made according to the procedure of Example 1, except that the ingredients are combined in the following concentrations by weight %:

| $KNO_3$ | 1% |
|---|---|
| Water | 10% |
| Polyethylene glycol | 80.8% |
| CARBOPOL 974P NF | 3.5% |
| Sodium hydroxide (50%) | 4.7% |

The foregoing procedure results in a sticky dental composition having reduced but significant desensitizing activity.

EXAMPLE 5

A dental composition within the scope of the present invention is made according to the procedure of Example 1, except that the ingredients are combined in the following concentration by weight %:

| $KNO_3$ | 7% |
|---|---|
| Water | 30% |
| Propylene glycol | 46.6% |
| CARBOPOL 974P NF | 7% |
| Sodium hydroxide (50%) | 9.4% |

The foregoing procedure results in a sticky dental composition having a high level of desensitizing activity.

EXAMPLE 6

A dental composition within the scope of the present invention is made according to the procedure of Example 1, except that the ingredients are combined in the following concentrations by weight %:

| $KNO_3$ | 10% |
|---|---|
| Water | 15% |
| Sorbitol | 65.6% |
| CARBOPOL 974P NF | 4% |
| Sodium hydroxide (50%) | 5.4% |

The foregoing procedure results in a sticky dental composition having a high level of desensitizing activity.

EXAMPLE 7

A dental composition within the scope of the present invention is made according to the procedure of Example 1, except that the ingredients are combined in the following concentrations by weight %:

| | |
|---|---|
| KNO₃ | 5% |
| Water | 5% |
| Polypropylene glycol | 77.3% |
| CARBOPOL 974P NF | 5% |
| Sodium hydroxide | 6.7% |
| Sodium EDTA | 0.5% |
| NaF | 0.5% |

The foregoing procedure results in a sticky dental composition having a moderate to high level of desensitization activity and a high level of anticariogenic activity.

EXAMPLE 8

A dental composition within the scope of the present invention is made according to the procedure of Example 1, except that the ingredients are combined in the following concentrations by weight %:

| | |
|---|---|
| KNO₃ | 2% |
| Glycerine | 42.9% |
| Polypropylene glycol | 50% |
| CARBOPOL 974P NF | 3% |
| Triethanolamine | 2% |
| Disodium EDTA | 0.1% |

The foregoing procedure results in a sticky dental composition that is combined with urea peroxide (10 wt %) just prior to treatment to yield a dental composition having bleaching activity as well as desensitizing activity.

EXAMPLE 9

To any of the foregoing dental compositions is added one or more of the following antimicrobial agents for treatment of a patient's gums: chlorhexadine, tetracycline, cetyl pyridinium chloride, benzalkonium chloride, cetyl pyridinium bromide, methyl benzoate, and propyl benzoate. These compositions are preferably used in conjunction with a thin walled, flexible dental tray that overlaps the person's gums in order for the dental compositions to contact the gums being treated.

EXAMPLE 10

A dental bleaching composition was prepared by combining the following ingredients:

| | |
|---|---|
| Carbamide Peroxide | 10% |
| Water | 21% |
| Glycerine | 57% |
| CARBOPOL 974P | 7% |
| Sodium hydroxide (50%) | 5% |

The CARBOPOL 974P was combined with the glycerine and then quickly mixed with the water. The glycerine enabled the CARBOPOL 974P to be dispersed in the water. The Carbamide peroxide was dissolved in the water before the glycerine-CARBOPOL 974P mixture was added to the water. The foregoing composition had a percentage of CARBOPOL 974P and water of about 25.7%. The sodium hydroxide was gradually blended into the homogenous composition in order to raise the pH to an acceptable level.

The foregoing procedure yielded a dental bleaching composition which was used to bleach a patient's teeth using the inventive passive-type dental trays of the present invention. The trays were worn by patients for nine hours. Subsequent examination of patient's teeth indicated that the teeth had whitened 1–1.5 units on a Vita shade guide and that significant quantities of this dental bleaching composition were still observed in the dental tray.

EXAMPLE 11

A dental bleaching composition within the scope of the present invention was made according to the procedure of Example 10, except that the ingredients were combined in the following amounts.

| | |
|---|---|
| Carbamide Peroxide | 10% |
| Water | 18% |
| Glycerine | 59% |
| CARBOPOL 974P | 7% |
| Sodium hydroxide (50%) | 6% |

EXAMPLE 12

A dental bleaching composition is made according to the procedure of Example 10, except that the ingredients are combined in the following amounts:

| | |
|---|---|
| Carbamide peroxide | 20% |
| Water | 20% |
| Glycerine | 40% |
| CARBOPOL 974P | 12% |
| Sodium hydroxide (50%) | 8% |

EXAMPLE 13

A dental bleaching composition is made according to the procedure of Example 10, except that the ingredients are combined in the following amounts:

| | |
|---|---|
| Carbamide peroxide | 5% |
| Water | 20% |
| Glycerine | 60% |
| CARBOPOL 974P | 10% |
| Sodium hydroxide (50%) | 5% |

EXAMPLE 14

A dental bleaching composition is made according to the procedure of Example 10, except that the ingredients are combined in the following amounts:

| | |
|---|---|
| Carbamide peroxide | 10% |
| Water | 40% |
| Glycerine | 30% |
| CARBOPOL 974P | 12% |
| Sodium hydroxide (50%) | 8% |

EXAMPLE 15

A dental bleaching composition is made according to the procedure of Example 10, except that the ingredients are combined in the following amounts:

| | |
|---|---|
| Carbamide peroxide | 18% |
| Water | 15% |
| Glycerine | 60% |

-continued

| | |
|---|---|
| CARBOPOL 974P | 4% |
| Sodium hydroxide (50%) | 3% |

EXAMPLE 16

A dental bleaching composition is made according to the procedure of Example 10, except that the ingredients are combined in the following amounts:

| | |
|---|---|
| Carbamide peroxide | 14% |
| Water | 10% |
| Glycerine | 60% |
| Polyethylene glycol | 11% |
| Carbopolyethylene 34P | 3% |
| Sodium hydroxide (50%) | 2% |

Although not a required ingredient, the polyethylene glycol assisted in mixing the ingredients together. However, it also diminished the flavor qualities somewhat.

EXAMPLE 17

A dental fluoride composition within the scope of the present invention was prepared by combining the following ingredients.

| | |
|---|---|
| Sodium fluoride | 1.1% |
| Water | 21.5% |
| Glycerine | 64.1% |
| CARBOPOL 974P | 2% |
| Sodium hydroxide (50%) | 5.1% |

The foregoing ingredients were mixed according to the procedure of Example 10, except that sodium fluoride was used instead of carbamide peroxide. The fluoride concentration yielded a free fluoride concentration of about 0.5%.

EXAMPLE 18

Any of the foregoing examples may be altered by substituting, or adding to, the active dental agent one or more of the following dental agents: chiorhexadine, tetracycline, cetyl pyridinium chloride, benzalkonium chloride, cetyl pyridinium bromide, methylbenzoate, and propylbenzoate.

EXAMPLE 19

To any of the foregoing dental compositions is added one of the following chelating agents: EDTA, monosodium EDTA, citric acid, succinic acid, and adipic acid.

In some cases, the sticky dental compositions may be used without a dental tray. For example, a sticky dental composition having an antimicrobial agent may be expressed directly into periodontal pockets. In such compositions, it would be preferred to maximize the carboxypolymethylene concentration and minimize the amount of added water so that the effects of saliva dilution are minimized. In addition, mucosal adhesive materials may be added to the composition to further assist in retaining the composition within the periodontal pocket. The prolonged activity of the dental agent within the sticky gel may last from hours to days, depending on the patient's oral and salival activity.

In summary, the present invention provides compositions for treating teeth and/or gums that are sufficiently sticky and resistant to dilution by saliva such that they have the ability to adhere and retain a flexible, thin-walled dental tray in place against a person's teeth, wherein the dental tray does not exert significant mechanical pressures onto the person's teeth or gums and is not designed to stay in place over the teeth due to mechanical fit.

The present invention further provides sticky dental compositions that allow for more secure and reliable contact between the active dental agent and a person's teeth and/or gums in order to provide more reliable and complete treatment of a person's teeth and/or gums.

In addition, the present invention provides dental compositions for treating teeth that can be adapted for use by disabled or semi-debilitated people who may not have strength, coordination or the ability to brush their teeth without the assistance of others.

The present invention also provides dental compositions that include a sticky matrix material that can be used in conjunction with a variety of dental agents for providing a variety of different treatments of a person's teeth and/or gums.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A sticky dental composition for treating a person's teeth, gums, or a combination thereof and adapted for use with a dental tray designed so as to not exert mechanical pressure on a person's teeth and gums, said composition comprising:

at least one dental agent selected from the group consisting of dental bleaching agents, anticariogenic agents, antimicrobial agents, and mixtures of the foregoing for providing a desired treatment of a person's teeth, gums, or a combination thereof; and a tackifying agent comprised of carboxypolymethylene, which includes any reaction products of carboxypolymethylene, the dental composition having a stickiness so that the dental composition is capable of adhering and retaining, for a length of time in order to carry out the desired treatment, a dental tray that is designed so as to not exert mechanical pressure onto the person's teeth and gums.

2. A sticky dental composition as defined in claim 1, wherein the dental agent comprises a bleaching agent selected from the group consisting of hydrogen peroxide and carbamide peroxide, and wherein the dental composition has a stickiness and resistance to dilution to saliva so that the dental composition is able to retain and hold the dental tray positioned over the person's teeth for a period of time of at least about one hour.

3. A sticky dental composition as defined in claim 1, wherein the carboxypolymethylene is added in an amount in a range from about 0.5% to about 20% by weight of the dental composition.

4. A sticky dental composition as defined in claim 1, wherein the carboxypolymethylene is added in an amount in a range from about 2% to about 12% by weight of the dental composition.

5. A sticky dental composition as defined in claim 1, wherein the carboxypolymethylene is added in an amount in a range from about 3% to about 10% by weight of the dental composition.

6. A sticky dental composition as defined in claim 1, wherein the dental composition further includes water in an amount up to about 50% by weight of the dental composition.

7. A sticky dental composition as defined in claim 1, wherein the dental composition further includes water in an amount in a range from about 2% to about 30% by weight of the dental composition.

8. A sticky dental composition as defined in claim 1, wherein the dental composition further includes a polyol.

9. A sticky dental composition as defined in claim 8, wherein at least a portion of the polyol include glycerin.

10. A sticky dental composition as defined in claim 9, wherein a portion of the polyol also includes polyethylene glycol.

11. A sticky dental composition as defined in claim 1, wherein the dental composition further includes a base added in an amount such that the dental composition has a pH in a range from about 4 to about 9.

12. A sticky dental composition as defined in claim 11, wherein the pH is in a range from about 5 to about 7.

13. A sticky dental composition as defined in claim 1, wherein the dental agent comprises an antimicrobial agent selected from the group consisting of chlorhexadine, tetracycline, cetyl pyridinium chloride, benzalkonium chloride, cetyl pyridinium bromide, methyl benzoate, and propyl benzoate.

14. A sticky dental composition as defined in claim 1, wherein the dental agent comprises an anticariogenic agent selected from the group consisting of sodium monofluorophosphate, sodium fluoride, and stannous fluoride.

15. A sticky dental composition as defined in claim 1, wherein the dental composition is pre-loaded within a syringe.

16. A sticky dental composition for treating a person's teeth gums, or a combination thereof and adapted for use with a flexible, thin-walled dental tray that is designed so as to not exert mechanical pressure on a person's teeth and gums, said dental composition comprising:
at least one dental agent for providing a desired treatment of a person's teeth gums, or a combination thereof, wherein the dental agent is selected from the group consisting of dental bleaching agents, anticariogenic agents, antimicrobial agents, and mixtures thereof; and
carboxypolymethylene, including any reaction products of carboxypolymethylene, included in an amount so that the dental composition is capable of adhering and retaining, for a length of time in order to carry out the desired treatment, a flexible, a thin-walled dental tray that is designed so as to not exert mechanical pressure onto the person's teeth and gums, the carboxypolymethylene being treated with a base so that the resulting dental composition has a pH in a range from about 5 to about 7.

17. A sticky dental composition as defined in claim 16, wherein the carboxypolymethylene is added in an amount in a range from about 2% to about 12% by weight of the dental composition.

18. A sticky dental composition for providing enhanced treatment of a person's teeth, gums, or a combination thereof in combination with a flexible, thin-walled dental tray that is designed so as to not exert mechanical pressure onto a person's teeth and gums, the sticky dental composition comprising:
at least one dental agent selected from the group consisting of dental bleaching agents, anticariogenic agents, antimicrobial agents, and mixtures thereof; and
a sticky matrix material into which the dental agent is dispersed, the matrix material including carboxypolymethylene and any reaction products of carboxypolymethylene, a polyol, a base, and optionally water in an amount in order that the resulting matrix material imparts to the dental composition a stickiness and resistance to dilution by saliva so that the dental composition is capable of adhering and retaining, for a period of time in order to carry out a desired treatment, a flexible, thin-walled dental tray that is designed so as to not exert mechanical pressure onto the person's teeth and gms, the base being included in an amount so that the resulting dental composition has a pH in a range from about 5 to about 7.

19. A system for treating a person's teeth or gums comprising:
a dental tray designed so as to not exert mechanical pressure onto the person's teeth and gums; and
a dental composition loaded within the dental tray and having a stickiness so that, when the dental tray is placed over the person's teeth, the dental composition adheres and retains the dental tray over the person's teeth for a period of time in order to carry out a desired treatment of the person's teeth, gums, or a combination thereof, the dental composition comprising:
at least one dental agent selected from the group consisting of dental bleaching agents, anticariogenic agents, antimicrobial agents, and mixtures of the foregoing; and
a tackifying agent comprised of carboxypolymethylene, inlcuding any reaction products of carboxypolymethylene.

20. A system as defined in claim 19, wherein the dental agent is a dental bleaching agent, and wherein the dental composition has a stickiness and resistance to dilution to saliva so that the dental composition is able to retain and hold the dental tray positioned over the person's teeth for a period of time of at least about one hour.

21. A sticky dental composition as defined in claim 13, wherein the dental composition has a stickiness and resistance to dilution to saliva so that the dental composition is able to retain and hold the dental tray positioned over the person's teeth for a period of time of at least about one hour.

22. A sticky dental composition as defined in claim 14, wherein the dental composition has a stickiness and resistance to dilution to saliva so that the dental composition is able to retain and hold the dental tray positioned over the person's teeth for a period of time of at least about one hour.

* * * * *

UNITED STATES PATENT AND TRADEMARK OFFICE
CERTIFICATE OF CORRECTION

PATENT NO. : 5,985,249
DATED : November 16, 1999
INVENTOR(S) : Dan E. Fischer

Page 1 of 2

It is certified that error appears in the above-identified patent and that said Letters Patent is hereby corrected as shown below:

Col. 1, ln. 6: after "part of" and before "U.S." insert --copending--

Col. 1, ln. 63: after "in order" delete [to]

Col. 1, ln. 64: before "bleaching" change "non-viscus" to --non-viscous--

Col. 2, ln. 32: before "are non-sticky" change "office" to --offices--

Col. 3, ln. 12: after "resistant to" change "dilation" to --dilution--

Col. 3, ln. 54: before "or other" change "triethanolarnine" to --triethanolamine--

Col. 3, ln 54: after "organic" change "anines" to --amines--

Col. 5, ln. 29: before "and complete" delete [more reliable]

Col. 7, ln. 25: after "dilution" change "to" to --by--

Col. 11, ln. 9: after "should be" change "counselled" to --counseled--

Col. 12, ln. 2 after "to act" and before "a glue" insert --as--

Col 12, ln. 6: after "they can" change "reliable" to --reliably--

Col 13, ln. 28: before "was first" change "NP" to --NF--

Col. 18, ln. 52: after "dilution" change "to" to --by--

UNITED STATES PATENT AND TRADEMARK OFFICE
CERTIFICATE OF CORRECTION

PATENT NO. : 5,985,249

DATED : November 16, 1999

INVENTOR(S) : Dan E. Fischer

It is certified that error appears in the above-identified patent and that said Letters Patent is hereby corrected as shown below:

Col. 20, ln. 21: after "and" change "gms" to --gums--

Col. 20, ln. 44: after "dilution" change "to" to --by--

Col 20, ln. 50: after "dilution" change "to" to --by--

Col. 20, ln. 55: after "dilution" change "to" to --by--

Signed and Sealed this

Fifth Day of September, 2000

Attest:

Q. TODD DICKINSON

Attesting Officer

Director of Patents and Trademarks